(12) United States Patent
Chehab et al.

(10) Patent No.: US 9,827,250 B2
(45) Date of Patent: Nov. 28, 2017

(54) LENS INCORPORATING MYOPIA CONTROL OPTICS AND MUSCARINIC AGENTS

(75) Inventors: Khaled Chehab, Jacksonville, FL (US); Arthur H. Shedden, Jr., Jacksonville, FL (US); Xu Cheng, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/563,322

(22) Filed: Jul. 31, 2012

(65) Prior Publication Data

US 2014/0036225 A1 Feb. 6, 2014

(51) Int. Cl.
*A61K 31/5513* (2006.01)
*A61K 31/46* (2006.01)
*G02C 7/04* (2006.01)

(52) U.S. Cl.
CPC .......... *A61K 31/5513* (2013.01); *A61K 31/46* (2013.01); *G02C 7/04* (2013.01); *G02C 7/041* (2013.01); *G02C 2202/24* (2013.01)

(58) Field of Classification Search
CPC ........ G02B 1/043; G02B 1/10; G02B 3/0037; G02B 7/02; G02C 7/04; G02C 2202/24; G02C 7/041; G02C 7/021; G02C 7/049; A61K 2300/00; A61K 31/46; A61K 31/5513; A61K 9/0048; A61K 9/0051; A61K 45/06; A61K 48/005
USPC .......... 623/5.11–6.62; 424/427–429; 351/159.01–159.81; 604/289–316
See application file for complete search history.

(56) References Cited

U.S. PATENT DOCUMENTS

| | | | |
|---|---|---|---|
| 3,901,967 A * | 8/1975 | Cohen et al. | 514/304 |
| 4,668,506 A | 5/1987 | Bawa | |
| 5,448,312 A | 9/1995 | Roffman et al. | |
| 5,691,323 A * | 11/1997 | Thompson et al. | 514/94 |
| 6,045,578 A | 4/2000 | Collins et al. | |
| 6,572,165 B2 * | 6/2003 | Faxe et al. | 294/1.2 |
| 6,822,016 B2 * | 11/2004 | McCabe et al. | 523/107 |

(Continued)

FOREIGN PATENT DOCUMENTS

| | | |
|---|---|---|
| CN | 1172644 A | 2/1998 |
| CN | 2430714 | 5/2001 |

(Continued)

OTHER PUBLICATIONS

Shih et al. "An intervention trial on efficacy of atropine and multi-focal glasses in controlling myopic progression", Jan. 15, 2002 Acta Ophthalmologica Scandinavica, vol. 79, Issue 3, Jan. 15, 2002, pp. 233-235 Copyright Acta Ophthalmol Scand 2001. ISSN 1395-3907.*

Chen, Zhi, et. al., "Effects of 0.05% Racanisodamine on Pupil Size and Accommodation", Optometry and Vision Science, vol. 87, No. 12, pp. 966-970 (2010).

(Continued)

*Primary Examiner* — Ricky Mack
*Assistant Examiner* — Daniele Manikeu
(74) *Attorney, Agent, or Firm* — Carl J. Evens

(57) ABSTRACT

Ophthalmic devices, such as contact lenses, may incorporate myopia control optics in combination with therapeutic agents also known to control myopia to create a drug delivery mechanism to inhibit or arrest the progression of myopia in individuals. Any number of contact lenses incorporating myopia control optics may be combined with a therapeutic agent such as atropine, atropine sulphate monohydrate, and/or pirenzepine.

5 Claims, 8 Drawing Sheets

(56) References Cited

U.S. PATENT DOCUMENTS

| | | |
|---|---|---|
| 7,625,086 B2 | 12/2009 | Wooley et al. |
| 7,637,612 B2* | 12/2009 | Menezes .................. 351/159.12 |
| 8,440,217 B1* | 5/2013 | El-Naggar et al. ........... 424/429 |
| 2004/0058357 A1* | 3/2004 | Soreg et al. ..................... 435/6 |
| 2005/0074497 A1 | 4/2005 | Schultz |
| 2005/0208102 A1 | 9/2005 | Schultz |
| 2005/0255144 A1 | 11/2005 | Schultz |
| 2006/0100408 A1 | 5/2006 | Powell et al. |
| 2006/0177483 A1* | 8/2006 | Byrne .................. A61K 9/0051 424/427 |
| 2007/0254914 A1* | 11/2007 | Wu et al. ...................... 514/304 |
| 2008/0100795 A1 | 5/2008 | Dubey |
| 2008/0124378 A1 | 5/2008 | Byrne et al. |
| 2008/0138408 A1* | 6/2008 | Venkatesh .............. A61K 31/70 424/464 |
| 2008/0194481 A1* | 8/2008 | Rosen .................... C07K 14/58 514/6.9 |
| 2008/0291393 A1 | 11/2008 | Menezes |
| 2009/0015786 A1* | 1/2009 | Harris .............. B29D 11/00317 351/159.64 |
| 2009/0141235 A1 | 6/2009 | Collins et al. |
| 2009/0303434 A1* | 12/2009 | Tung ............................. 351/161 |
| 2010/0073629 A1 | 3/2010 | Menezes |
| 2010/0114309 A1* | 5/2010 | de Juan et al. .............. 623/6.39 |
| 2010/0195044 A1 | 8/2010 | Collins et al. |
| 2010/0209477 A1* | 8/2010 | Butuner et al. ............... 424/427 |
| 2010/0239637 A1* | 9/2010 | Ciolino ................. A61F 9/0017 424/429 |
| 2010/0328604 A1 | 12/2010 | Collins et al. |
| 2011/0040376 A1* | 2/2011 | Christie et al. .............. 623/6.17 |
| 2011/0046033 A1* | 2/2011 | Zhang .................... A01N 25/02 510/112 |
| 2011/0059902 A1* | 3/2011 | Sullivan ............... A61K 9/0048 514/20.8 |
| 2011/0249234 A1 | 10/2011 | Duis |
| 2013/0314665 A1 | 11/2013 | Tung |

FOREIGN PATENT DOCUMENTS

| | | |
|---|---|---|
| CN | 1642578 A | 7/2005 |
| CN | 101344648 A | 1/2009 |
| CN | 101688983 A | 3/2010 |
| EP | 219207 A2 | 4/1987 |
| EP | 2639627 A1 | 9/2013 |
| JP | 6206820 A | 7/1994 |
| JP | 2005523299 A | 8/2005 |
| JP | 2008529606 A | 8/2008 |
| JP | 2009132671 A | 6/2009 |
| JP | 2010528339 A | 8/2010 |
| SG | 193699 A1 | 10/2013 |
| WO | WO 03/077952 A1 | 9/2003 |
| WO | WO 2003077952 A1 | 9/2003 |
| WO | WO 06/084275 A2 | 8/2006 |
| WO | WO 2006084275 A2 | 8/2006 |
| WO | WO 08/060574 A2 | 5/2008 |
| WO | WO 09/045172 A1 | 4/2009 |
| WO | WO 10/083129 A9 | 7/2010 |

OTHER PUBLICATIONS

Iuvone, P., et al, "Effects of Apomorphine, a Dopamine Receptor Agonist, On Ocular Refraction and Axial Elongation in a Primate Model of Myopia", Investigative Ophthalmology & Visual Science, vol. 32, No. 5, pp. 1674-1677 (Apr. 1991).

Anstice, N., et al., "Effect of Dual-Focus Soft Contact Lens Wear on Axial Myopia Progression in Children", Ophthalmology, J., vol. 118, No. 6, pp. 1152-1161.

Ashby, R., et al., "The Effect of Ambient Illuminance on the Development of Deprivation Myopia in Chicks", Investigative Ophthalmology & Visual Science, vol. 50, No. 11, pp. 5348-5354 (2009).

European Search Report for Application No. EP13178603 dated Oct. 24, 2013.

Written Report from the Intellectual Property Office of Singapore for Application No. 2013056866 dated Oct. 17, 2014.

* cited by examiner

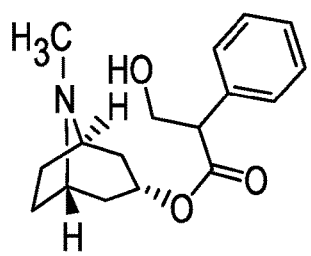
FIG. 1A

FIG. 2
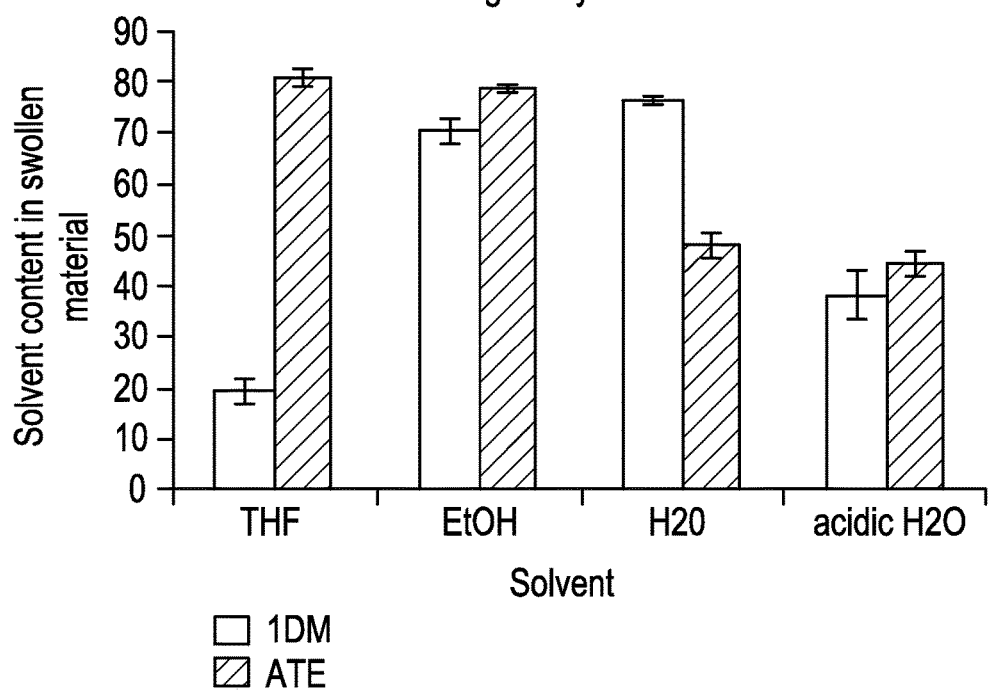

LENS INCORPORATING MYOPIA CONTROL OPTICS AND MUSCARINIC AGENTS

BACKGROUND OF THE INVENTION

1. Field of the Invention

The present invention relates to ophthalmic lenses, and more particularly, to ophthalmic lenses designed to slow, retard or prevent myopia progression. The ophthalmic lenses of the present invention comprise myopia control optics in combination with muscarinic agents, including atropine, atropine sulphate monohydrate and pirenzepine, to create an effect for increased myopia progression control.

2. Discussion of the Related Art

Myopia or nearsightedness is an optical or refractive defect of the eye wherein rays of light from an image focus to a point before they reach the retina. Myopia generally occurs because the axial length of the eyeball globe is too long or the anterior surface of the cornea is too steep. Myopia affects up to thirty-three (33) percent of the population of the United States and in some parts of the world, up to seventy-five percent of the population. The cause of this refractive error is unknown; however, it is most likely due to a combination of genetic and environmental factors. A minus powered spherical lens may be utilized to correct myopia. The minus powered lens diverges the incoming light rays thereby moving the focal point of the image back onto the macula. As set forth herein, these corrective lenses treat myopia, but do not prevent the progression of myopia.

A number of methods to slow or retard myopia progression, especially in children, have been proposed and developed. These methods including utilizing multi-focal lenses, utilizing lenses with one or more aberrations introduced therein, utilizing lenses which control aberrations, utilizing off axis power lenses, reshaping the cornea, exercising the eye and utilizing pharmacological or drug therapies.

The use of multi-focal lenses and those having aberrations have proved to be somewhat disadvantageous in that the lenses may compromise the wearer's distance vision and have limited treatment efficacy of around thirty (30) percent to fifty (50) percent of axial elongation or refractive difference to age matched control group as shown in a number of published studies. The other methods set forth above also suffer from disadvantages, including discomfort, as with the corneal reshaping, and potentially undesirable side effects, as with the pharmacological or drug therapies. Specifically, atropine, a non-selective muscarinic agent, has been shown in a number of studies to be useful in the treatment of myopia.

Accordingly, there exists a need for a therapy for at least one of inhibiting, preventing and/or controlling the progression of myopia that combines the benefits of one or more individual therapies in order to achieve a desired effect while minimizing the disadvantages of currently available therapies.

SUMMARY OF THE INVENTION

The contact lens incorporating myopia control optics and selective or non-selective muscarinic agents of the present invention overcomes a number of disadvantages associated with the prior art.

In accordance with one aspect, the present invention is directed to an ophthalmic lens for at least one of inhibiting, preventing and/or controlling myopia progression. The ophthalmic lens comprises a contact lens formed from a first material and incorporating myopia control optics, and an antimuscarinic agent incorporated into a mixture being at least one of affixed to or incorporated into the first material forming the contact lens, the antimuscarinic agent being configured to elute into the eye over a predetermined period of time.

Hundreds of millions of people around the world wear corrective lenses such as glasses or contact lenses to correct refractive error of their eyes. Refractive error is caused by a distortion of the cornea and/or a mismatch of the eyeball's focal length with the eye's refractive power. For example, a steeper cornea or an excessively long axial length of the eyeball causes myopia, a flatter cornea or a short axial length of the eyeball causes hyperopia, and an irregular or toroidal curved cornea causes astigmatism. The current standard treatment for these refractive errors involves wearing corrective lenses such as contact lenses or glasses. More aggressive treatment for these refractive errors include eye surgery which may involve reshaping of the cornea utilizing laser ablation or insertion of a phakic intraocular lens, thereby providing the patient with improved vision. However, these devices, techniques and/or procedures only address the symptoms of these refractive errors or deviations and do not correct the axial elongation of the globe and the subsequent increase in myopia. These surgical interventions also may pose significant adverse event risks. In addition, even with correction via any of these devices and/or techniques, genetic and environmental influences, for example, excessive near focus activities, including computer work and video games and lack of outdoor activities, may have further negative impact on the growth of the eye. In other words, myopia continues to develop and/or worsen.

The present invention is directed to a combination contact lens product, made of a hydrogel material such as etafilcon A or a silicon hydrogel such as narafilcon A and/or narafilcon B, galyfilcon A or senofilcon A that incorporates myopia control optics, multifacial/bifocal optics, single vision optics, and/or astigmatic optics with a selective or non-selective pharmacological agent such as atropine, atropine sulphate monohydrate, pirenzepine and/or similar function compounds aimed at least one of inhibiting, preventing and/or controlling the progression of myopia.

More particularly, to capitalize on pharmacological effects and thus increased patient acceptance as well as an increased myopia control treatment outcome, a number of selective or non-selective antagonist compounds, including those set forth above, may be used at smaller and safer doses, for example, at between 0.0005 to 0.5 mg per contact lens which corresponds to 0.002 to 0.83 weight percent of the lens, in combination with myopia control optics. A particular advantage of the lenses of the present invention is increased treatment efficacy, due to the synergistic effects between the optics and the therapeutic agent, while maintaining acceptable and functional accommodation with minimal or no visual artifacts that is resultant of pupil dilation when these therapeutic agents are utilized at doses higher than 0.5 percent in solution which corresponds to 0.25 mg of therapeutic agent applied to the eye.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 1A and 1B represent the chemical structures of atropine sulphate monohydrate and atropine respectively.

FIG. 2 is a graphical representation of various solvents in both ACUVUE® TrueEye® Brand Contact Lenses and 1-DAY ACUVUE® MOIST® Brand Contact Lenses in accordance with the present invention.

DETAILED DESCRIPTION OF THE PREFERRED EMBODIMENTS

Figure 1B:
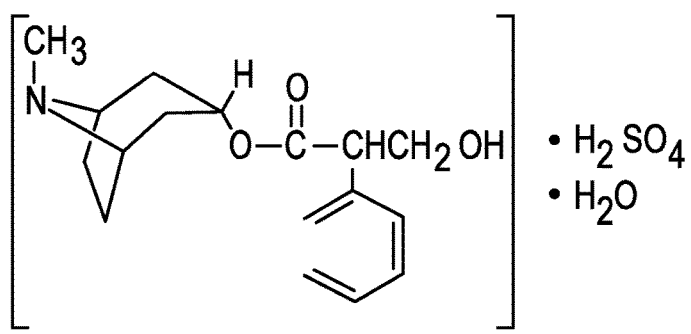

The present invention relates to the incorporation of a therapeutic agent, for example, atropine and/or pirenzepine, at moderate to low levels, for example, less than 0.25 mg/lens of the contact lens, in a myopia control contact lens to effectively slow or stop myopia progression. Atropine is a naturally occurring tropane alkaloid and is classified as a non-selective antimuscarinic agent that works by blocking muscarinic receptors that are found in the muscles of the eye and which are involved in controlling the size of the pupil and the shape of the lens. Atropine, by ocular instillation, has been demonstrated in studies to be useful for the treatment of myopia. Ocular instillation of atropine results in delivery of the drug to the systemic circulation and risk of associated adverse effects such as tachycardia, elevated body temperature and agitation. Accordingly, a preferable method of delivery may be via a contact lens. More specifically, a combination contact lens product, made of a hydrogel material such as etafilcon A or a silicon hydrogel such as narafilcon A or B, galyfilcon A or senofilcon A that incorporate myopia control optics with a selective or non-selective antagonist agent such as atropine, or similar function compounds, to slow or stop the progression of myopia. Essentially, it is believed that the combination of myopia control drugs, at low doses, along with the myopia control optics will have desirable effects that will result in greater treatment efficacy with reduced potential side effects from either the optics or drugs individually. Furthermore, since the patient will benefit from the refractive correction of myopia provided by the optics of the device, compliance may be improved in comparison to topical instillation of a pharmacological agent such as atropine.

It is important to understand the terminology in the description of the exemplary embodiments of the present invention. For example, if the therapeutic agent is set forth as 1 weight percent, this is its concentration in solution, which in turn corresponds to 0.5 mg of therapeutic agent that is exposed to the eye, which in turn corresponds to 1.66 weight percent of the drug in the contact lens or 0.5 mg/lens for an etafilcon A lens which weighs about 30 mg. Accordingly, if the therapeutic agent is set forth as 0.5 weight percent, this is its concentration in solution, which in turn corresponds to 0.25 mg of therapeutic agent that is exposed to the eye, which in turn corresponds to 0.83 weight percent of the drug in the contact lens or 0.25 mg/lens, and if the therapeutic agent is set forth as 0.01 weight percent, this is its concentration in solution, which in turn corresponds to 0.005 mg of therapeutic agent that is exposed to the eye, which in turn corresponds to 0.016 weight percent of the drug in the contact lens or 0.005 mg/lens.

In accordance with the present invention, a therapeutic agent such as atropine, which is available in two forms; namely, atropine and atropine sulphate monohydrate, may be dissolved in appropriate solvent or solvent system such as tetrahydrofuran (THF) and water (1/3, v/v), ethanol (EtOH) and water (1/1, v/v), acidic water with a pH<2, glycerol, or preferably buffered saline solution. The drug/solvent mixture may then be incorporated into the contact lens. To incorporate the drug/solvent into the contact lens, de-ionized water rinsed lenses may be placed in a container, for example, the blister package, with a buffered saline solution comprising atropine and/or atropine sulphate monohydrate in a concentration ranging from about 0.001 weight percent to about 0.50 weight percent in solution. Once the contact lenses are positioned in the solution in the blister package, the blister package is sealed and sterilized. The lenses in the blister package uptake the drug over a period of time ranging from about one (1) hour to about forty-eight (48) hours. Once the contact lenses are placed on the eyes of the patient, the atropine and/or atropine sulphate monohydrate elutes from the lenses over a given period of time. The material forming the lenses as well as any additional coatings placed on the lenses determines the mechanism and timing of how the drug is uploaded.

There are a number of contact lenses that may be utilized for the prevention or retardation of myopia progression. For example, in U.S. Pat. No. 7,637,612 to Menezes, it is disclosed that myopia progression can be substantially prevented by providing a multifocal lens having an area of distance vision power in the center of the optic zone surrounded by at least one region that provides positive longitudinal spherical aberration. This at least one region of the lens provides positive longitudinal spherical aberrations that continuously and progressively increases as one moves from the boundary of the region closest to the optical center of the lens to the outermost boundary of the region.

Orthokeratology is the practice of fitting contact lenses which are designed to deliberately alter the shape of the central cornea. By making the central cornea flatter in curvature, the optical power of the cornea decreases. This has the effect of reducing the degree of myopia of the eye. Specifically designed rigid contact lenses are typically worn overnight and removed in the morning. The pressure exerted by the rigid lens on the cornea temporarily flattens the central cornea. This flattening leads to a reduction of myopia which gradually regresses over the next one to three days. The lenses are worn every one to three days. Studies have shown that patients wearing orthokeratology lenses not only have a reduction in myopia, but a reduction in the rate of myopia progression. U.S. Patent Application Publication No. 2010/0328604 to Collins et al. discloses lenses designed using corneal topography or wavefront measurements of the eye derived by subtracting the optical power of the eye after orthokeratology treatment from optical power before orthokeratology treatment and thus may be utilized to slow the progression of myopia. Each lens comprises a central optic zone surrounded by a peripheral zone further surrounded by an edge zone and a concave surface which sits on the wearer's eye. The lens power at any location in the optical zone is derived by subtracting the optical power of the eye after orthokeratology treatment from the optical power before orthokeratology treatment to derive the optical power at each location in the zone.

U.S. Patent Application Publication No. 2010/0195044 to Collins et al. discloses the design of lenses using wavefront measurements amenable to correction factors for near and far vision as well as pupil size to slow or stop myopia progression. In this invention, each lens comprises a convex surface with a central optic zone surrounded by a peripheral zone which is further surrounded by an edge zone, and a concave surface which rests on the patient's eye. The lens power at any location in the optical zone is described by the sum of the apical distance averaged wavefront derived power plus a correction which is derived from a single, partial multiple, or multiple of the difference between the distance and near average wavefront derived power at each location and the difference between the apical near and distance wavefront derived powers. Further refinement of the design can be based on the pupil size. The natural pupil size for near accommodation levels is typically smaller than that for distance accommodation levels. Therefore, for an optical design based on foveal vision (on-axis), the change in optical power required to control eye growth based on the near wavefront can be confined to an optical zone diameter corresponding to the smaller pupil present when the near wavefront is measured. Outside of this inner central region, the optical design can revert to one that is relevant for distance vision.

U.S. Pat. No. 6,045,578 to Collins et al. discloses a method of treatment and prevention of myopia by inducing positive spherical aberration. The cornea of a myopic eye is fitted with a lens having its outer surface formed with increased dioptric power away from the axis of the lens and cornea. Paraxial light rays entering the central portion of the lens are focused on the retina producing a clear image of an object. Marginal light rays entering the peripheral portion of the cornea are focused in a plane between the cornea and the retina and produce positive spherical aberration of the image on the retina. This positive spherical aberration produces a physiological effect on the eye which tends to inhibit growth of the eye, thus mitigating the tendency for the eye to grow longer.

U.S. Patent Application Publication No. 2009/0141235 to Collins et al. discloses a means for controlling the progression of myopia by at least partially counteracting certain forces acting on the eye by the eyelids that are associated with myopia and myopic progression. Dispersing eyelid forces encompasses both absorbing and redirecting the forces applied to the eye by at least one of the upper and lower eyelids. Dispersing of eyelid forces includes dispersing the forces that would otherwise be applied by at least one of the upper and lower eyelids to an eye to the contact lens which absorbs the forces rather than the eye. Dispersion of eyelid forces also includes the redistribution of forces that would otherwise be applied by at least one of the upper and lower eyelids to the eye to an object that is not the eye and to an area of the eye that does not influence myopia. Many material properties may be exploited to disperse eyelid forces, including but not limited to, thickness, modulus, elastomeric properties, pneumatic properties and hydraulic properties. Dispersing forces applied to the eye by the upper and lower eyelids may be achieved by globally thickening the lens, or by thickening the lens in one or more defined regions. An alternative to lens thickening is to alter the modulus of the lens material, again regionally or globally or in one or more defined regions. The modulus of the lens material is altered to a higher or lower value.

U.S. Pat. No. 5,448,312 to Roffman et al. discloses a multifocal contact lens design which consists of concentric spherical annular zones for distance vision and for near vision, which are meant to be viewed simultaneously by the visual system. The presence of the near zones substantially reduces the accommodative effort for a wearer in order to be able to focus the eye for near objects.

U.S. Pat. No. 7,625,086 to Wooley et al. discloses a multifocal contact lens design and method which consists of concentric aspherical annular zones for distance vision and for near vision, which are meant to be viewed simultaneously by the visual system. The presence of the near zones substantially reduces the accommodative effort for a wearer in order to be able to focus the eye for near objects.

As set forth above, there are a number of contact lens designs that may be utilized in combination with a therapeutic agent to prevent or slow the progression of myopia. Experiments set forth below illustrate the feasibility of incorporating an agent such as atropine and/or atropine sulphate monohydrate into a contact lens. While the drug would normally be loaded into a contact lens comprising myopia control optics, the experiments described below utilize two different types of lenses in order to demonstrate the various parameters and results of drug loading. The two types of lenses utilized are the ACUVUE® TrueEye® Brand Contact Lens (ATE) and the 1-DAY ACUVUE® MOIST® Brand Contact Lens (1 DAM). The ATE lens comprises narafilcon B, a silicone hydrogel polymer, and the 1-Day lens comprises etafilcon A, a high water content ionic hydrogel polymer and polyvinylpyrrolidone (PVP). The chemical structure of both atropine sulphate monohydrate and atropine, which are utilized in the experiments, are illustrated in FIGS. 1A and 1B respectively. Ultraviolet spectrophotometry at a wavelength of 257 nm was utilized to analyze all the samples.

In order to determine suitable solvents for loading the atropine and/or atropine sulphate monohydrate into the contact lenses, swelling in various solvents known to dissolve the atropine and/or atropine sulphate monohydrate, was performed. It is important to note that water is a preferred solvent; however, it may be necessary to load in and/or utilize alternate solvents. The lenses were washed in water for three (3) days with three (3) changes of the water in order to remove any salt present as a result of storage in the buffer. The lenses were then dried in a thirty seven (37) degree C. oven for forty-eight (48) hours and weighed. Three repeats were performed on each lens. The lenses were swollen in various solvents, including those set forth above, and the uptake of the solvent was determined after the swelling period by determining the swollen mass of the lens. Solvent content was determined based on the equation given by $$\text{Solvent content} = \frac{\text{Swollen mass} - \text{Dry mass}}{\text{Swollen mass}} \times 100\%.$$

The approximate solubility of the two drugs, atropine (AT) and atropine sulphate monohydrate (ATSM) was evaluated in the various solvents. Essentially, a given solvent was added slowly to a known amount of the drug and an approximate solubility was determined.

Based on the swelling and the solubility studies, ethanol/water and THF/water (1:3 v/v) were used to load the ATSM and AT into the lenses respectively. For loading, the lenses were washed in water and were dried as in the swelling study. The dried lenses were weighed and placed into the loading solutions shown below in Table 1. The lenses remained in the drug solution for a period of forty-eight (48) hours at four (4) degrees C. Following loading, the lenses were dried and reweighed to determine the quantity of drug taken up. Amounts of drug taken up in the lenses for the different loading solutions are summarized in Table 2, given below, for the 1 DAM lenses and Table 3, given below, for the ATE lenses. Note that aside from the atropine sulphate monohydrate which was loaded at a considerably higher level in the 1 DAM lenses, similar amounts were loaded into the two lens types irrespective of the loading method. However, to some extent, the loading method may be used to control the amount of drug in the lens as is explained in more detail subsequently.

TABLE 1

Drug loading solutions

| | |
|---|---|
| loading solution 1: | Atropine sulphate monohydrate 250 mg/ml in water |
| loading solution 2: | Atropine 20 mg/ml in THF/water(1/3, v/v) |
| loading solution 3: | Atropine 20 mg/ml in EtOH/water(1/1, v/v) |
| loading solution 4: | Atropine 10 mg/ml in acidic water(pH < 2) |
| control: | contact lenses only, no drug loaded |

TABLE 2

Drug loading into DAM lenses

| Sample | Drug Loaded (mg/lens) |
|---|---|
| 1DAM-1 | 11.96 |
| 1DAM-2 | 3.64 |
| 1DAM-3 | 5.74 |
| 1DAM-4 | 0.48 |

TABLE 3

Drug loading into ATE lenses

| Sample | Drug Loaded (mg/lens) |
|---|---|
| ATE-1 | 4.10 |
| ATE-2 | 4.06 |
| ATE-3 | 3.26 |
| ATE-4 | 0.46 |

The drug loaded lenses were characterized for transparency and lysozyme adsorption in order to determine whether there were changes in the lens properties and lens interactions with the presence of the drug. For transparency, the absorbance was measured spectrophotometrically between 350 and 700 nm. Protein adsorption measurements were performed using 125-I labeled lysozyme. Protein adsorption was determined after zero (0), two (2) and eight (8) hours of drug release. Transmission electron microscopy or TEM analysis was also performed to assess the drug dispersion in the matrix.

Five drug loaded lenses, all together, were placed into 1 mL of phosphate buffered saline (PBS) and placed in a shaking water bath at thirty-four (34) degrees C. Samples were taken at regular intervals and replaced with fresh PBS. Release samples were analyzed spectrophotometrically to determine the concentration. As well, the nature of the peaks was also examined to determine whether there were any changes relative to the control samples (freshly prepared drug in appropriate buffer solutions). Drug loading and release was controlled using different loading concentrations to determine whether the release rate of the drug could be altered by changing simply or easily controlled conditions. Various drug concentrations were examined. In the case of the ATE lenses, ATSM in water at various concentrations was examined or utilized as set forth in Table 4. In the case of 1 DAM, AT in ethanol and water (1:1) at various concentrations was examined or utilized. For the ATSM release from ATE lenses, the lenses were removed from the loading solution and rinsed to remove loosely physically adsorbed drug. For the 1 DAM lenses, the lenses were dried to remove any residual ethanol and rehydrated prior to the release study.

TABLE 4

Concentrations used for determining effect of loading concentration

| Lens Type | Drug | Loading concentration (mg/mL) |
|---|---|---|
| ATE | ATSM | 250 |
| ATE | ATSM | 100 |
| ATE | ATSM | 50 |
| ATE | ATSM | 10 |
| 1DAM | AT | 20 |
| 1DAM | AT | 10 |
| 1DAM | AT | 5 |
| 1DAM | AT | 2 |

In addition, it may be desirable to use the lenses on a repeated basis for the release of the drug. Accordingly, the ATE lenses were loaded and depleted of drug and then reloaded on a repeated basis to determine whether the release kinetics were similar following a single release. The second loading occurred in a 250 mg/mL solution of ATSM in water overnight at four (4) degrees C. Loaded lenses were dipped in PBS to remove any loosely adsorbed drug and then released into PBS at thirty-seven (37) degrees C.

The results of the solvent content study are illustrated in FIG. 2. As may be seen in the figure, the 1 DAM lenses swell well in both ethanol and water, while not surprisingly based on the silicone content, the ATE lenses show good swelling in both THF and ethanol, with moderate swelling in water.

The solubility results are set forth in Table 5 below. There are clear differences in the solubility of the two forms of atropine, with no solvent showing a clear trend to dissolving both drugs. Of note, the sulphate monohydrate form of the drug shows much higher solubility in the solvents in general and the aqueous solvents in particular, while the unmodified form of the drug is more soluble in THF and ethanol. Note that while glycerol showed good drug solubility, it was clear that this solvent would be difficult to ultimately remove from the lenses and therefore it was not used. For drug loading, mixtures of THF and water and ethanol and water (1:3, v/v) were utilized in order to balance the need for high swelling with desired drug solubility.

TABLE 5

Solubility result summary

| Solvent type | Atropine solubility Mg/ml | ATSM solubility Mg/ml |
|---|---|---|
| THF | ~150 | Very low |
| EtOH | ~250 | ~200 |
| Glycerol | ~10 | ~400 |
| $H_2O$ | ~2.0 | ~2500 |
| PBS | ~2.5 | ~800 |
| Acidic water (pH 1.9) | ~12.5 | Not tested |

Figure 3A:
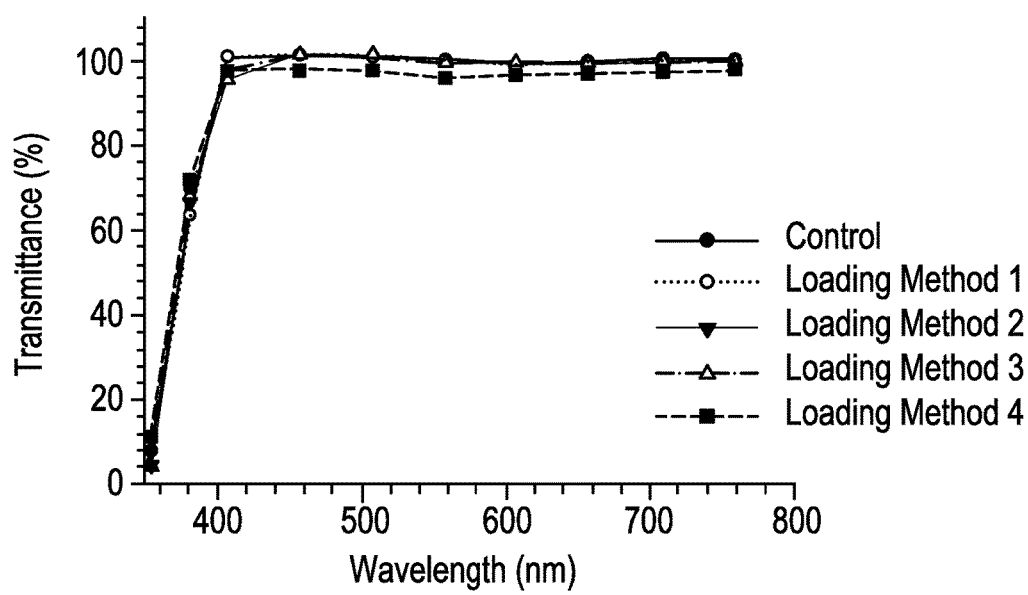
FIG. 3A graphically illustrates the relationship between transmittance and wavelength for drug loaded 1-DAY ACUVUE® MOIST® Brand Contact Lenses in accordance with the present invention.
Figure 3B:
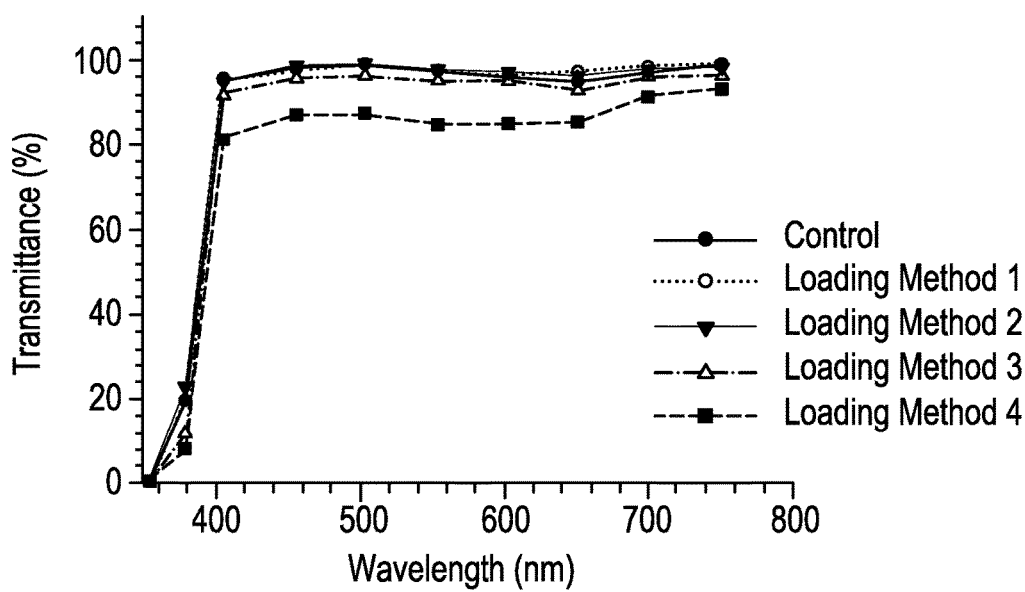
FIG. 3B graphically illustrates the relationship between transmittance and wavelength for drug loaded ACUVUE® TrueEye® Brand Contact Lenses in accordance with the present invention.

Transparency results, which are summarized in FIGS. 3A and 3B, demonstrate no changes in the transparency of either lens material when loaded with the different drug solvent combinations relative to the control. Therefore, it is clear that neither the presence of the atropine or the atropine sulphate monohydrate has a negative effect on the transparency of the lens material. It is important to note; however that there was a slight decrease in transparency when the ATE lenses were loaded using an acidic solution.

Figure 4A:
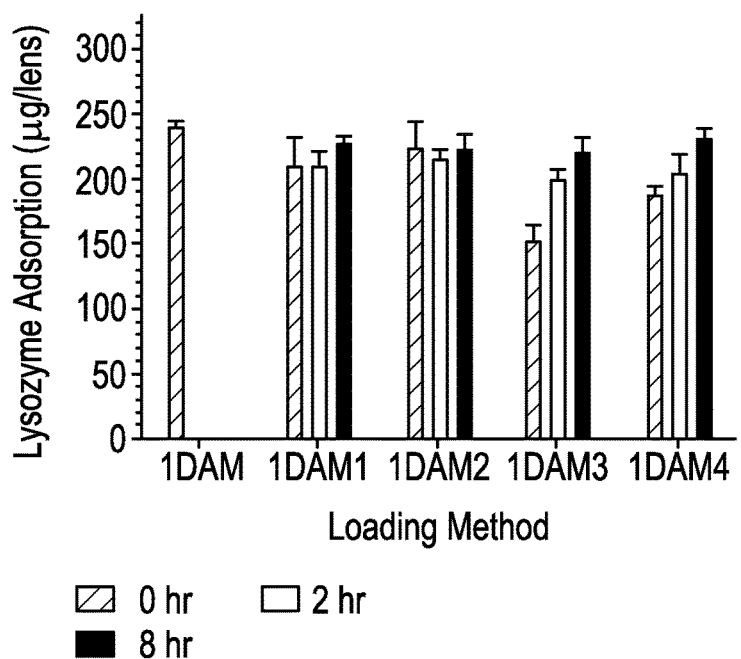
FIG. 4A graphically illustrates lysozyme absorption in drug loaded 1-DAY ACUVUE® MOIST® Brand Contact Lenses in accordance with the present invention.
Figure 4B:
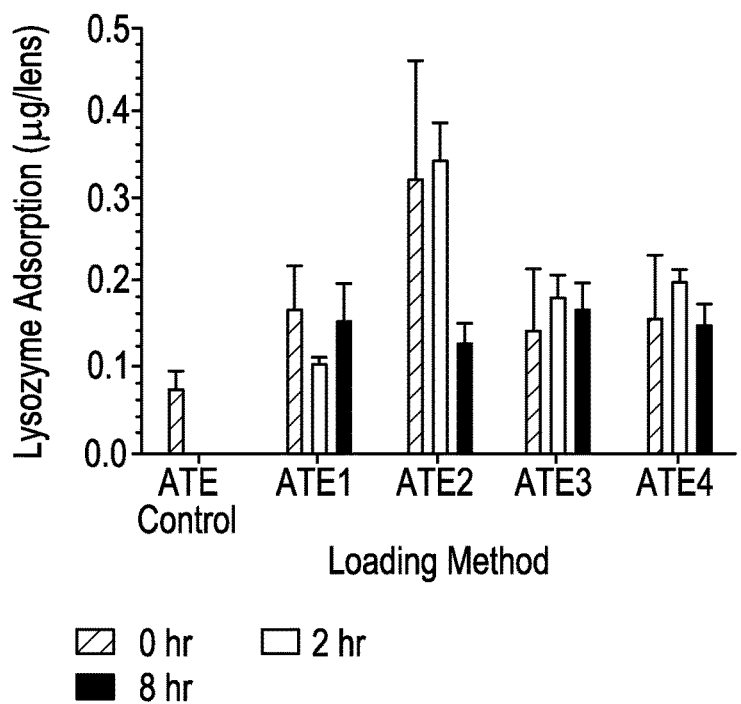
FIG. 4B graphically illustrates lysozyme absorption in drug loaded ACUVUE® TrueEye® Brand Contact Lenses in accordance with the present invention.

Protein (lysozyme) adsorption results are illustrated in FIGS. 4A and 4B. Not surprisingly, the 1 DAM lenses took up more protein in general than the ATE lenses. There were some slight changes in the protein adsorption with the presence of the drug depending on the loading method examined For example, the 1 DAM lenses showed decreased lysozyme adsorption initially when loaded in either ethanolic or acidic solutions but the levels of lysozyme associated with the lenses increased with the release of the drug. There was a trend to increased levels of protein associated with the ATE lenses at all release times and with all loading methods relative to the controls. It is unknown at this time whether these increases were the result of exposure to the loading solvents or whether they were due to the presence of the drug. While there are slight differences in the 1 DAM lenses with the presence of the atropine and the atropine sulphate monohydrate, they are relatively small and appear to be solvent dependent. However, with the ATE lenses, there is an increase in lysozyme uptake when the presence of the drug in general that is observed at all release times.

It is important to note that Transmission Electron Microscopy or TEM analysis of all the samples demonstrated a uniform dispersion of drug particles within the matrix.

To establish drug release concentrations, five drug loaded lenses were placed into 1 ml of phosphate buffered saline (PBS) solution and placed in a shaking water bath at 34° C. The 1 ml solution was taken at regular intervals and replaced with fresh PBS solution. Samples of solution were analyzed spectrophotometrically to determine the concentration of the released drug.

Figure 5:
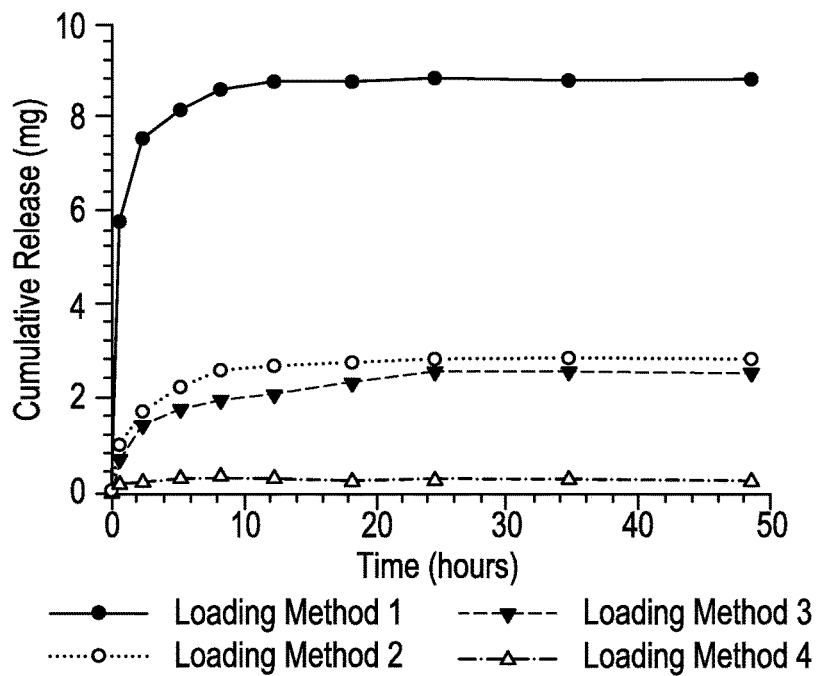
FIG. 5 graphically illustrates long term drug release from drug loaded 1-DAY ACUVUE® MOIST® Brand Contact Lenses in accordance with the present invention.
Figure 6:
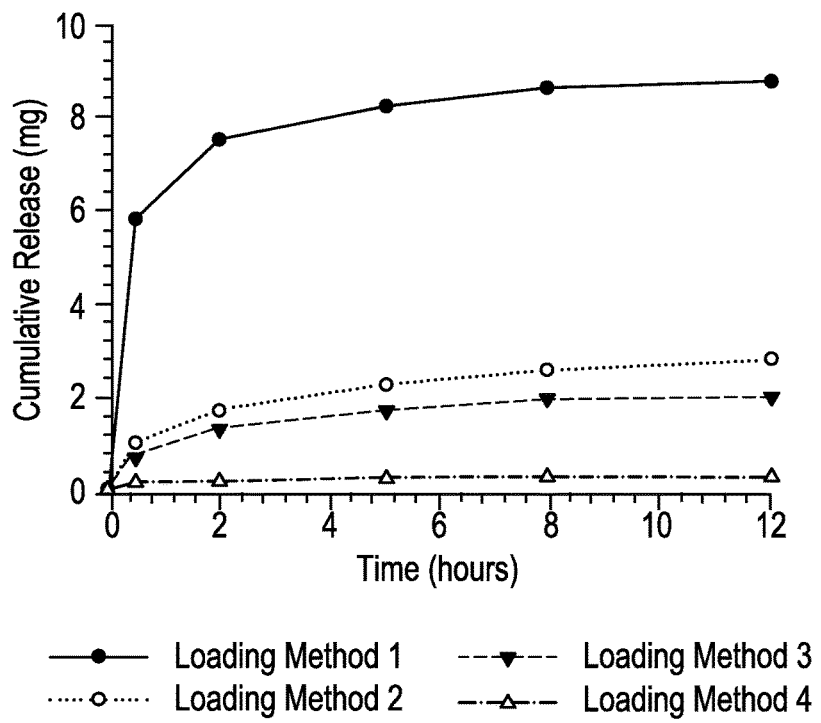
FIG. 6 graphically illustrates short term drug release from drug loaded 1-DAY ACUVUE® MOIST® Brand Contact Lenses in accordance with the present invention.

FIG. 5 illustrates the slow or non-burst release of AT and ATSM from 1 DAM lenses and FIG. 6 illustrates the burst period release of AT and ATSM from 1 DAM lenses. The results shown in FIG. 5 for release from 1 DAM lenses demonstrate that the more hydrophilic ATSM molecules release more quickly in greater amounts. Measureable release occurred over periods of more than sixty (60) hours. Release in all cases was typified by a rapid burst followed by a relatively slow gradual release.

Figure 7:
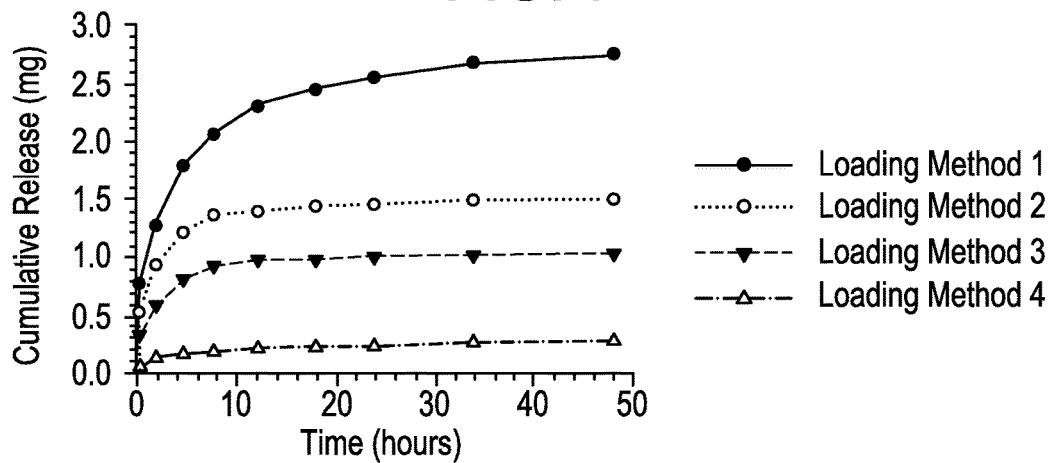
FIG. 7 graphically illustrates long term drug release from drug loaded ACUVUE® TrueEye® Brand Contact Lenses in accordance with the present invention.
Figure 8:
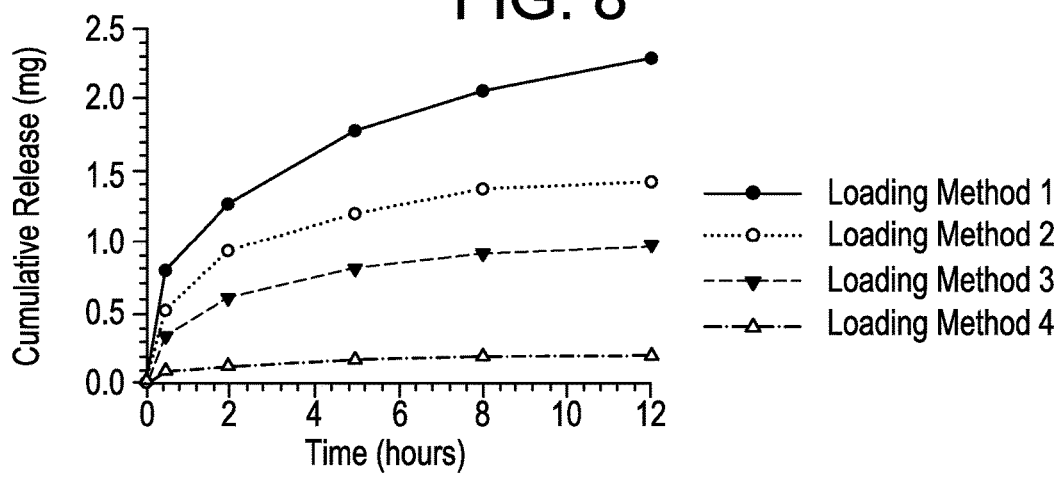
FIG. 8 graphically illustrates short term drug release from drug loaded ACUVUE® TrueEye® Brand Contact Lenses in accordance with the present invention.
Figure 9:
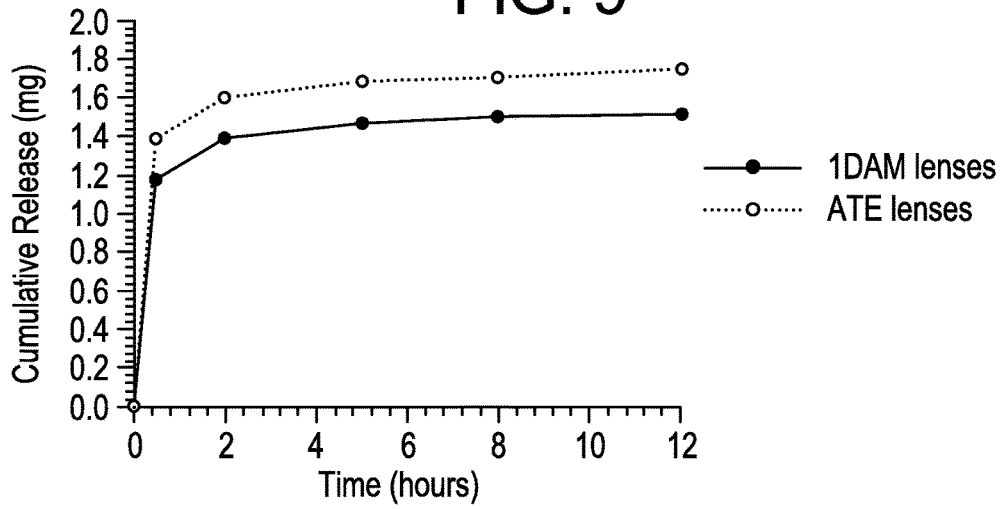
FIG. 9 graphically illustrates the cumulative release of atropine over a twelve hour period from both ACUVUE® TrueEye® Brand Contact Lenses and 1-DAY ACUVUE® MOIST® Brand Contact Lenses loaded from acid conditions in accordance with the present invention.

FIG. 7 illustrates the slow or non-burst release of AT and ATSM from ATE lenses and FIG. 8 illustrates the burst period release of AT and ATSM from ATE lenses. As illustrated in FIG. 7, a somewhat lower release rate of the ATSM was achieved utilizing the ATE lenses as compared to the 1 DAM lenses. In other words, it can be seen from a comparison of the figures that lower amounts of the drugs were released from the ATE lenses despite the fact that the drug loadings were approximately the same. In addition, after a small initial burst, relative constant release of all molecules from the ATE lenses was achieved and despite the fact that the ATE lenses took up almost the same amount of AT and ATSM, release was slower over a period of daily wear.

Highly acidic solutions were examined as a means of increasing drug loading/controlling release from the lenses. Results are illustrated for the release of AT loaded in a 25 mg/mL solution in HCl. It may be seen that the release is relatively unaffected by this loading and therefore this is not likely an effective method of altering the release kinetics. Release in this case was characterized by an extremely high burst, presumably due to the crystallization of the drug on the surface of the lens. There were no real differences between the two lens types.

Figure 10A:
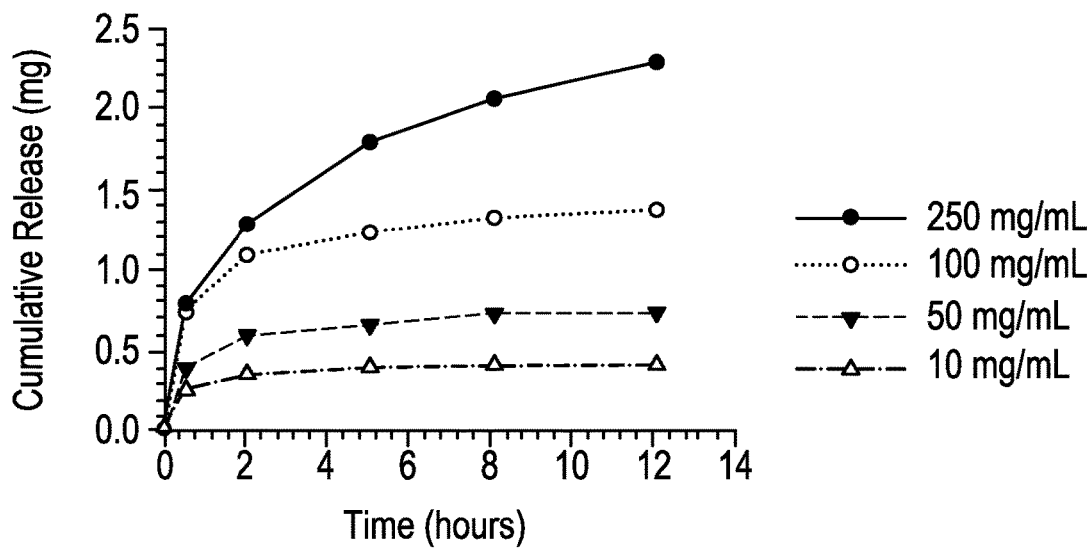
FIG. 10A graphically illustrates the cumulative release of atropine sulphate monohydrate in varying concentrations from ACUVUE® TrueEye® Brand Contact Lenses in accordance with the present invention.
Figure 10B:
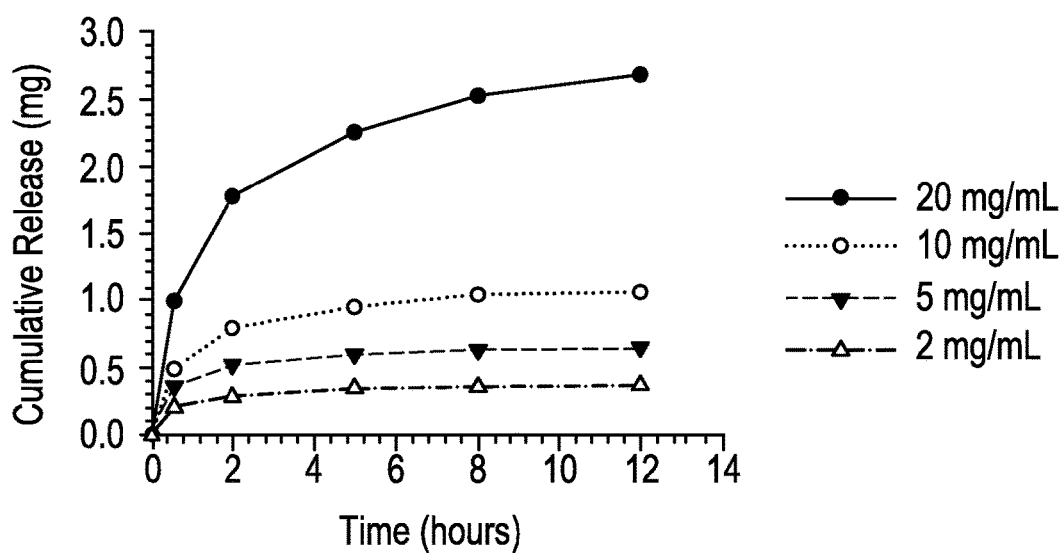
FIG. 10B graphically illustrates the cumulative release of atropine in varying concentrations from 1-DAY ACUVUE® MOIST® Brand Contact Lenses in accordance with the present invention.

FIG. 10A illustrates the release rates of ATSM from ATE lenses with loading solution concentrations between 250 mg/mL and 10 mg/mL while FIG. 10B illustrates the release rates of AT from 1 DAM lenses with loading solution concentrations between 20 mg/mL and 5 mg/mL. It can be seen from FIGS. 10A and 10B that controlling the release rate of the atropine and the atropine sulphate monohydrate using the simple technique of altering the loading concentration is possible. Clearly, obtaining physiologically relevant concentrations in the eye may be achieved relatively easily by simple changes.

As briefly set forth above, 0.5 percent atropine drops that are instilled one (1) time per day show efficacy in slowing the progression of myopia. Assuming a 50 μL drop volume and one (1) drop instilled with each installation, the corresponding amount of atropine instilled into the eye each day is approximately 0.5 mg. However, as much as ninety-five percent (95) of this volume is lost as with the instillation of all drops. In addition, it can also be assumed that as much as eighty percent (80) of drug is lost when delivered from contact lenses. Therefore based on these assumptions, a total of between 0.0005 and 0.50 mg of drug must be delivered from the contact lens. Therefore, it is clear that the amounts released from this lens are appropriate for the treatment using atropine.

Figure 11A:
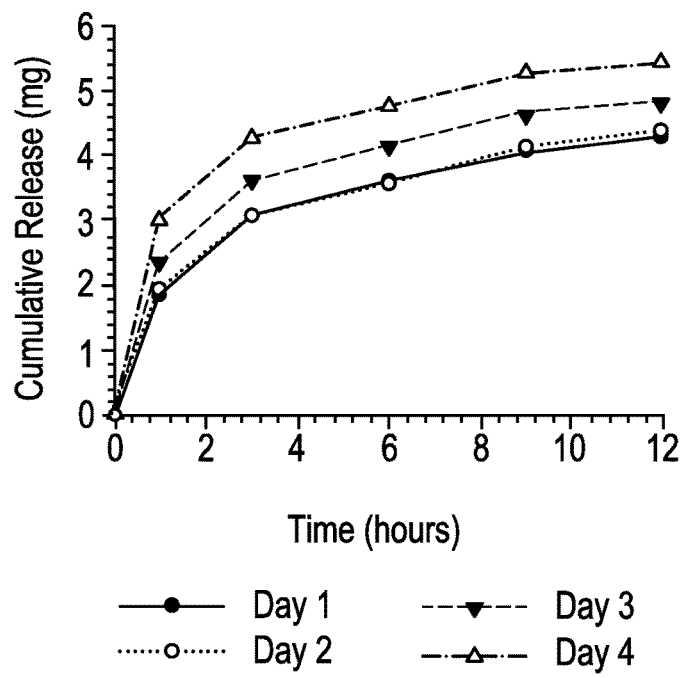
FIG. 11A graphically illustrates the cumulative release of atropine sulphate monohydrate soaked ACUVUE® TrueEye® Brand Contact Lenses in accordance with the present invention.
Figure 11B:
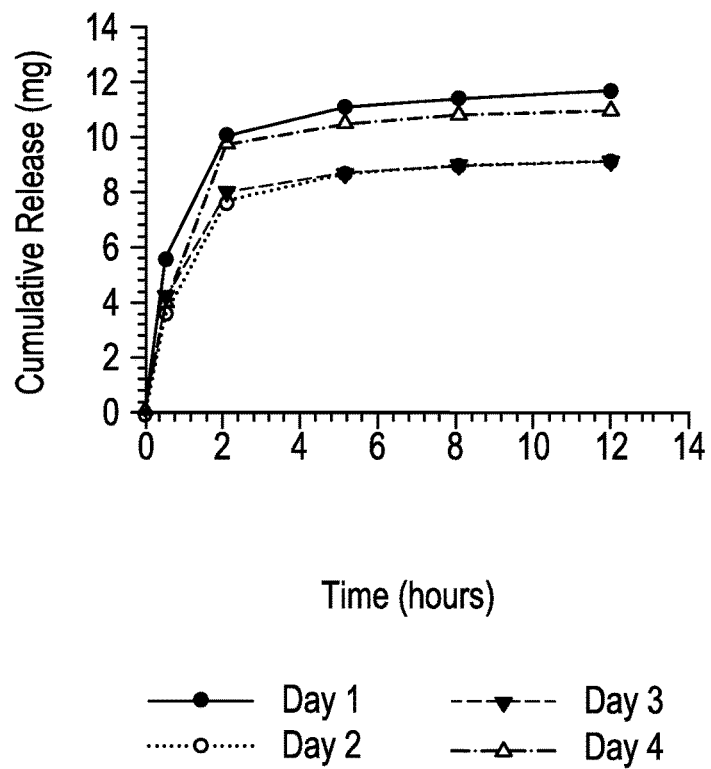
FIG. 11B graphically illustrates the cumulative release of atropine sulphate monohydrate soaked 1-DAY ACUVUE® MOIST® Brand Contact Lenses in accordance with the present invention.

Release from the contact lenses over periods of days with swelling in ATSM solutions from ATE lenses and 1 DAM lenses are illustrated in FIGS. 11A and 11B respectively. Clearly, in both cases, the lenses can be swollen in solutions of atropine and release the drug. This may be a potentially appropriate method of delivering the drugs.

Based on the results of these experiments, it seems that the release of both atropine and atropine sulphate monohydrate from daily wear contact lenses represents a promising method of delivering the drug. Drug release kinetics from both versions of the daily wear lenses tested could be adjusted to give therapeutically relevant concentrations of the drug in the release medium. There were no changes in the chemical structure of the drug with uptake and release as shown by UV analysis. Likely however the most interesting result was the ability of the drug to be taken up by the lenses with subsequent swelling in aqueous solutions and released with the same kinetics. This suggests that it may be possible that release from reusable lenses is also possible. In other words, a patient may be given a solution of the therapeutic agent to soak the contact lens in for a given period of time and then reuse the lens.

Figure 12:
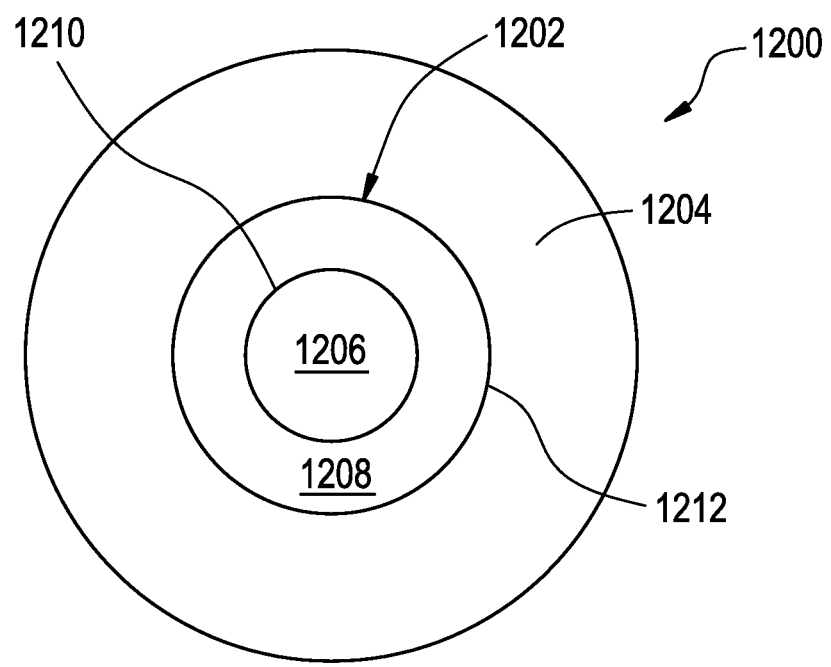
FIG. 12 is a diagrammatic representation of an ophthalmic lens comprising myopia control optics.

As described above, U.S. Pat. No. 7,637,612 to Menezes describes a lens with myopia control optics. FIG. 12 illustrates the exemplary lens of Menezes.

FIG. 12 illustrates a lens 1200 that has an optic zone 1202 and a non-optical, lenticular zone 1204. Optic zone 1202 comprises a central zone 1206 and peripheral zone 1208. Central zone 1206 is centered at the optical axis of the lens and has a radius of about 0.5 to 2 mm and preferably about 1 to 1.5 mm measured from the optical center of the lens. The power within central zone 1206 is substantially constant distance vision power and will be about −0.50 diopters to about −12.00 diopters. Due to the addition of the positive power in the peripheral zone 1208, it may be desirable to provide overcorrection for the distance vision power in the central zone 1206, meaning power in addition to that required to correct the wearer's distance vision acuity. The amount of overcorrection will depend upon the diameter of the central zone 1206 and the magnitude of the positive spherical aberration provided. However, typically, the overcorrection will be about 0.25 to about 1.00 diopters.

Peripheral zone 1208 provides positive longitudinal spherical aberration that continuously and progressively increases as one moves from the innermost boundary 1210, or boundary closest to the optical center of the lens, to the outermost boundary 1212 of the peripheral zone 1208. The increase in longitudinal spherical aberration in peripheral zone 1208 may be about 0.25 to about 2 diopters, and preferably is about 0.5 to about 1.50 diopters, at a radius of about 2.5 mm from the optical center of the lens. Peripheral zone 1208 may have a width of about 0.5 to about 3.5 mm, preferably about 1 to about 2 mm.

As shown in FIG. 12, central zone 1206 and peripheral zone 1208 are zones with discrete junctions therebetween. In an alternate embodiment, no discrete junction exists between the substantially constant distant vision power and the positive longitudinal spherical aberration, both the substantially constant distant vision power and the positive longitudinal spherical aberration forming one zone.

In designing the lenses of the invention, the positive longitudinal spherical aberration is induced beyond the correction of the wearer's ocular aberrations. Thus, for purposes of the invention, preferably the spherical aberration of the lens wearer is first determined and then the spherical aberration necessary to correct that aberration is provided. Alternatively, a population average, such as 0.1 D/mm$^2$ may be used for the spherical aberration. Spherical aberration may be measured by any known and convenient method including, without limitation, by use of a commercially available aberrometer.

Any of a number of mathematical functions may be used to design the optic zone of the lenses of the invention including, without limitation, spheres, aspheres, splines, conics, polynomials and the like. In a preferred embodiment, the central zone preferably is spherical and there is a smooth transition between the central and peripheral zone. Such a smooth transition may be ensured by use of mathematical functions that are continuous in magnitude and first and second derivatives.

Although atropine, atropine sulphate monohydrate and pirenzepine are described herein, other agents in the class of anti-muscarinic agents may be utilized. For example, other anti-muscarinic agents, including racanisodamine, cyclopentolate, homatropine, scopolamine, telenzepine, nuvenzepine and rispenzepine may be utilized in accordance with the present invention. In addition, other classes of drugs or therapeutic agents may also be utilized in accordance with the present invention, for example, dopamine agonists, including apomorphine, bromocriptine, quinpirole and levodopa.

The above-described invention is directed to ophthalmic lenses, specifically contact lenses, which comprise myopia progression optics in combination with muscarinic agents, including atropine and atropine sulphate monohydrate to create synergistic effect for increase myopia progression control. It is, however, important to note that ophthalmic lenses, specifically contact lenses, may be utilized to deliver a wide range of therapeutic agents. For example, the contact lenses may be configured to deliver various drug formulations, medications and/or active agents for the one or more of the treatment, inhibition, and prevention of numerous diseases and disorders. The contact lenses may be used to deliver mydriatics and cycloplegics including atropine sulphate, homatropine, scopolamine HBr, cyclopentolate HCl, tropicamide, and phenylephrine HCl. The contact lenses may be configured to deliver azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The contact lenses may be used to deliver mast cell stabilizers, for example, cromolyn sodium, lodoxamide tromethamine, nedocromil sodium, and permirolast potassium. The contact lenses may be used to deliver corticosteroids including dexamethasone sodium phosphate, dexamethasone, fluoromethalone, fluoromethalone acetate, loteprednol etabonate, prednisolone acetate, prednisolone sodium phosphate, medrysone, rimexolone, and fluocinolone acetonide. The contact lenses may be used to deliver non-steroidal anti-inflammatory agents including flurbiprofen sodium, suprofen, diclofenac sodium, ketorolac tromethamine, cyclosporine, rapamycin methotrexate, azathioprine, and bromocriptine. The contact lenses may be used to deliver anti-infective agents including tobramycin, moxifloxacin, ofloxacin, gatifloxacin, ciprofloxacin, gentamicin, sulfisoxazolone diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine. The contact lenses may be used to deliver agents for the one or more of the treatment, inhibition, and prevention of glaucoma including epinephrines, including dipivefrin; alpha-2 adrenergic receptors, including aproclonidine and brimonidine; betablockers including betaxolol, carteolol, levobunolol, metipranolol, and timolol; direct miotics, including carbachol and pilocarpine; cholinesterase inhibitors, including physostigmine and echothiophate; carbonic anhydrase inhibitors, including acetazolamide, brinzolamide, dorzolamide, and methazolamide; prostoglandins and prostamides including latanoprost, bimatoprost, uravoprost, unoprostone cidofovir and travoprost. The contact lenses may be used to deliver antiviral agents, including fomivirsen sodium, foscarnet sodium, ganciclovir sodium, valganciclovir HCl, trifluridine, acyclovir, and famciclovir. The contact lenses may be used to deliver local anesthetics, including tetracaine HCl, proparacaine HCl, proparacaine HCl and fluorescein sodium, benoxinate and fluorescein sodium, and benoxnate and fluorexon disodium. The contact lenses may be used to deliver antifungal agents, including fluconazole, flucytosine, amphotericin B, itraconazole, and ketocaonazole. The contact lenses may be used to deliver analgesics including acetaminophen and codeine, acetaminophen and hydrocodone, acetaminophen, ketorolac, ibuprofen, and tramadol. The contact lenses may be used to deliver vasoconstrictors including ephedrine hydrochloride, naphazoline hydrochloride, phenylephrine hydrochloride, tetrahydrozoline hydrochloride, and oxymetazoline. The contact lenses may also be used to deliver vitamins, antioxidants, and nutraceuticals including, vitamins A, D, and E, lutein, taurine, glutathione, zeaxanthin, fatty acids and the like.

It is important to note that the contact lens may incorporate additional materials or agents that function to reduce any potential bright light visual disturbances that may be associated with any of the therapeutic agents described herein. For example, a photochromic agent may be incorporated into the lens to reduce bright light visual disturbances. In another alternate exemplary embodiment, a neutral filter dye may be incorporated into the lens to reduce bright light visual disturbances.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens system for at least one of inhibiting, preventing and/or controlling myopia progression, the ophthalmic lens system comprising:
   a contact lens formed from at least one of a hydrogel or silicon hydrogel material and incorporating myopia control optics and one or more of single vision optics, astigmatism optics, bifocal optics, and multifocal optics, the contact lens including an optic zone having a central zone surrounded by at least one region that is configured to provide positive longitudinal spherical aberrations that continuously and progressively increase away from the center of the lens, the central zone including between 0.25 and 1.00 diopters of additional distance power correction; a blister package that contains the contact lens; and
   a solution within the blister package; the solution comprising atropine sulphate monohydrate and buffered saline infused via swelling into the contact lens in an amount sufficient to deliver between 0.0005 and 0.5 mg of atropine sulphate monohydrate to a patient's eye over the course of a single day with a cumulative delivery having a profile of an initial burst of up to about 2 mg within the first hour, up to 3 mg within the next hour and up to about 4 mg over the next 9 hours; the solution chemically structured to create synergistic effect to increase myopia progression control.

2. The ophthalmic lens for at least one of inhibiting, preventing and/or controlling myopia progression according to claim 1, further comprises a photochromic agent incorporated into the contact lens.

3. The ophthalmic lens for at least one of inhibiting, preventing and/or controlling myopia progression according to claim 1, further comprises a neutral filter dye incorporated into the contact lens.

4. The ophthalmic lens for at least one of inhibiting, preventing and/or controlling myopia progression according to claim 1, wherein the contact lens comprises a daily wear lens.

5. The ophthalmic lens for at least one of inhibiting, preventing and/or controlling myopia progression according to claim 1, wherein the contact lens comprises a reusable lens.

* * * * *